US009011511B2

(12) United States Patent
Gregorich et al.

(10) Patent No.: US 9,011,511 B2
(45) Date of Patent: Apr. 21, 2015

(54) BALLOON CATHETER

(75) Inventors: Daniel J. Gregorich, Plymouth, MN (US); Eric Petersen, Maple Grove, MN (US); Adam D. Grovender, Brooklyn Park, MN (US); David D. Groneberg, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 847 days.

(21) Appl. No.: 12/709,258

(22) Filed: Feb. 19, 2010

(65) Prior Publication Data

US 2011/0009942 A1 Jan. 13, 2011

Related U.S. Application Data

(60) Provisional application No. 61/154,339, filed on Feb. 20, 2009.

(51) Int. Cl.
*A61F 2/06* (2013.01)
*A61M 25/10* (2013.01)
(Continued)

(52) U.S. Cl.
CPC .............. *A61M 25/104* (2013.01); *A61F 2/856* (2013.01); *A61F 2/954* (2013.01); *A61F 2/958* (2013.01); *A61F 2250/0029* (2013.01); *A61M 25/0051* (2013.01); *A61M 25/0052* (2013.01); *A61M 25/0053* (2013.01); *A61M 25/0054* (2013.01);
(Continued)

(58) Field of Classification Search
CPC .................................... A61F 2/958; A61F 2/95
USPC .................................. 623/1.11, 1.35; 600/435
See application file for complete search history.

(56) References Cited

U.S. PATENT DOCUMENTS 4,762,129 A  8/1988 Bonzel
4,917,666 A  4/1990 Solar et al.
(Continued)

FOREIGN PATENT DOCUMENTS

EP  1084728  3/2001
EP  1374943  1/2004
(Continued)

OTHER PUBLICATIONS

Terumo Corporation Press Release, "New Release of Terumo PTCA Catheter RX-2 (pet name "Ryujin Plus"), a Device for use in the Treatment of Angina and Myocardial Infarction," Jan. 7, 2005, 2 pages.
(Continued)

*Primary Examiner* — Thomas J Sweet
*Assistant Examiner* — Seema Mathew
(74) *Attorney, Agent, or Firm* — Seager, Tufte & Wickhem LLC

(57) ABSTRACT

Balloon catheters and stent delivery systems including bifurcated stent delivery systems are disclosed. An example bifurcated stent delivery system may include an elongate shaft including a proximal section, a midshaft section, and a distal section. The proximal section may include a tubular member having a plurality of slots formed therein. The slots may be arranged in one or more sections having differing slot densities. The midshaft section may include a guidewire port in fluid communication with a guidewire lumen formed in the shaft. A main branch balloon may be coupled to the shaft. A side branch balloon may be disposed adjacent to the main branch balloon. A stent may be disposed on the main branch balloon and on the side branch balloon.

12 Claims, 8 Drawing Sheets

(51) Int. Cl.
*A61F 2/954* (2013.01)
*A61F 2/958* (2013.01)
*A61M 25/00* (2006.01)
*A61F 2/856* (2013.01)
*A61M 25/01* (2006.01)

(52) U.S. Cl.
CPC ... *A61M 25/1011* (2013.01); *A61M 2025/0183* (2013.01); *A61M 2025/1056* (2013.01)

(56) References Cited

U.S. PATENT DOCUMENTS

| | | | |
|---|---|---|---|
| 4,998,923 A | 3/1991 | Samson et al. | |
| 5,040,548 A | 8/1991 | Yock | |
| 5,095,915 A | 3/1992 | Engelson | |
| 5,156,594 A * | 10/1992 | Keith | 604/103.09 |
| 5,217,482 A | 6/1993 | Keith | |
| 5,242,396 A | 9/1993 | Evard | |
| 5,279,562 A | 1/1994 | Sirhan et al. | |
| 5,300,025 A | 4/1994 | Wantink | |
| 5,322,505 A | 6/1994 | Krause et al. | |
| 5,346,505 A | 9/1994 | Leopard | |
| 5,387,193 A | 2/1995 | Miraki | |
| 5,439,447 A | 8/1995 | Miraki | |
| 5,458,613 A | 10/1995 | Gharibadeh et al. | |
| 5,477,856 A | 12/1995 | Lundquist | |
| 5,480,382 A | 1/1996 | Hammerslag et al. | |
| 5,490,837 A | 2/1996 | Blaeser et al. | |
| 5,496,294 A | 3/1996 | Hergenrother et al. | |
| 5,507,751 A | 4/1996 | Goode et al. | |
| 5,507,766 A | 4/1996 | Kugo et al. | |
| 5,522,818 A | 6/1996 | Keith et al. | |
| 5,542,434 A | 8/1996 | Imran et al. | |
| 5,573,520 A | 11/1996 | Schwartz et al. | |
| 5,626,593 A | 5/1997 | Imran | |
| 5,634,902 A | 6/1997 | Johnson et al. | |
| 5,658,251 A | 8/1997 | Ressemann et al. | |
| 5,690,613 A | 11/1997 | Verbeek | |
| 5,702,439 A | 12/1997 | Keith et al. | |
| 5,720,724 A | 2/1998 | Ressemann et al. | |
| 5,743,876 A | 4/1998 | Swanson | |
| 5,807,355 A | 9/1998 | Ramzipoor et al. | |
| 5,810,867 A | 9/1998 | Zarbatany et al. | |
| 5,823,995 A | 10/1998 | Fitzmaurice et al. | |
| 5,876,375 A | 3/1999 | Penny | |
| 5,882,336 A | 3/1999 | Janacek | |
| 5,911,715 A | 6/1999 | Berg et al. | |
| 5,957,903 A | 9/1999 | Mirzaee et al. | |
| 5,980,484 A | 11/1999 | Ressemann et al. | |
| 5,980,486 A | 11/1999 | Enger | |
| 6,004,291 A | 12/1999 | Ressemann et al. | |
| 6,013,069 A | 1/2000 | Sirhan et al. | |
| 6,014,919 A | 1/2000 | Jacobsen et al. | |
| 6,022,343 A | 2/2000 | Johnson et al. | |
| 6,024,722 A | 2/2000 | Rau et al. | |
| 6,030,405 A | 2/2000 | Zarbatany et al. | |
| 6,039,699 A | 3/2000 | Viera | |
| 6,048,338 A | 4/2000 | Larson et al. | |
| 6,066,114 A | 5/2000 | Goodin et al. | |
| 6,066,144 A | 5/2000 | Wolf et al. | |
| 6,102,890 A | 8/2000 | Stivland et al. | |
| 6,107,004 A * | 8/2000 | Donadio, III | 430/320 |
| 6,129,708 A | 10/2000 | Enger | |
| 6,152,909 A | 11/2000 | Bagaoisan et al. | |
| 6,190,358 B1 | 2/2001 | Fitzmaurice et al. | |
| 6,193,686 B1 | 2/2001 | Estrada et al. | |
| 6,238,430 B1 * | 5/2001 | Klumb et al. | 623/1.11 |
| 6,246,914 B1 | 6/2001 | de la Rama et al. | |
| 6,273,879 B1 | 8/2001 | Keith et al. | |
| 6,299,595 B1 * | 10/2001 | Dutta et al. | 604/96.01 |
| 6,344,029 B1 | 2/2002 | Estrada et al. | |
| 6,368,316 B1 * | 4/2002 | Jansen et al. | 604/526 |
| 6,409,863 B1 * | 6/2002 | Williams et al. | 156/198 |
| 6,428,849 B1 | 8/2002 | Jacobsen et al. | |
| 6,440,088 B1 | 8/2002 | Jacobsen et al. | |
| 6,447,479 B1 | 9/2002 | Nobuyoshi et al. | |
| 6,488,655 B1 | 12/2002 | Wantink et al. | |
| 6,524,300 B2 | 2/2003 | Meglin | |
| 6,533,754 B1 | 3/2003 | Hisamatsu et al. | |
| 6,548,010 B1 | 4/2003 | Stivland et al. | |
| 6,553,880 B2 | 4/2003 | Jacobsen et al. | |
| 6,575,958 B1 | 6/2003 | Happ et al. | |
| 6,579,246 B2 | 6/2003 | Jacobsen et al. | |
| 6,585,718 B2 * | 7/2003 | Hayzelden et al. | 604/523 |
| 6,589,207 B1 | 7/2003 | El-Nounou | |
| 6,592,569 B2 | 7/2003 | Bigus et al. | |
| 6,605,057 B2 | 8/2003 | Fitzmaurice et al. | |
| 6,623,448 B2 | 9/2003 | Slater | |
| 6,635,029 B1 | 10/2003 | Venturelli | |
| 6,648,854 B1 * | 11/2003 | Patterson et al. | 604/96.01 |
| 6,679,909 B2 * | 1/2004 | McIntosh et al. | 623/1.11 |
| 6,695,812 B2 | 2/2004 | Estrada et al. | |
| 6,733,487 B2 | 5/2004 | Keith et al. | |
| 6,746,423 B1 | 6/2004 | Wantink | |
| 6,749,560 B1 * | 6/2004 | Konstorum et al. | 600/143 |
| 6,887,219 B2 | 5/2005 | Wantink | |
| 6,890,318 B2 | 5/2005 | Wantink | |
| 6,953,470 B2 * | 10/2005 | Holman et al. | 606/194 |
| 7,001,358 B2 | 2/2006 | Fitzmaurice et al. | |
| 7,037,291 B2 | 5/2006 | Lee et al. | |
| 7,169,162 B2 | 1/2007 | Garakani | |
| 7,195,611 B1 | 3/2007 | Simpson et al. | |
| 7,294,124 B2 | 11/2007 | Eidenschink | |
| 7,344,557 B2 | 3/2008 | Yadin | |
| 7,367,967 B2 | 5/2008 | Eidenschink | |
| 7,604,621 B2 | 10/2009 | Eidenschink | |
| 7,655,030 B2 | 2/2010 | Williams et al. | |
| 7,708,704 B2 * | 5/2010 | Mitelberg et al. | 600/585 |
| 7,780,626 B2 * | 8/2010 | Wu et al. | 604/96.01 |
| 8,021,329 B2 * | 9/2011 | Griffin et al. | 604/96.01 |
| 8,369,935 B2 * | 2/2013 | Ryan | 600/424 |
| 8,414,568 B2 | 4/2013 | Harlan | 606/15 |
| 8,795,202 B2 * | 8/2014 | Northrop et al. | 600/585 |
| 2001/0029362 A1 | 10/2001 | Sirhan et al. | |
| 2001/0037085 A1 | 11/2001 | Keith et al. | |
| 2002/0077594 A1 * | 6/2002 | Chien et al. | 604/103.02 |
| 2003/0004540 A1 | 1/2003 | Linder et al. | |
| 2003/0055447 A1 | 3/2003 | Lee et al. | |
| 2003/0069522 A1 | 4/2003 | Jacobsen et al. | |
| 2003/0105427 A1 | 6/2003 | Lee et al. | |
| 2003/0176837 A1 | 9/2003 | Fitzmaurice et al. | |
| 2004/0059292 A1 | 3/2004 | Hisamatsu et al. | |
| 2004/0181174 A2 | 9/2004 | Davis et al. | |
| 2004/0230178 A1 | 11/2004 | Wu | |
| 2004/0249436 A1 | 12/2004 | Aznoian et al. | |
| 2005/0049552 A1 | 3/2005 | Holzapfel et al. | |
| 2005/0059959 A1 | 3/2005 | Eidenschink | |
| 2005/0102019 A1 | 5/2005 | Yadin | |
| 2005/0149159 A1 * | 7/2005 | Andreas et al. | 623/1.11 |
| 2005/0177132 A1 * | 8/2005 | Lentz et al. | 604/525 |
| 2005/0216018 A1 * | 9/2005 | Sennett | 606/79 |
| 2005/0267444 A1 | 12/2005 | Griffin et al. | |
| 2006/0004346 A1 * | 1/2006 | Begg | 604/525 |
| 2006/0064074 A1 | 3/2006 | Mallaby | |
| 2006/0100687 A1 * | 5/2006 | Fahey et al. | 623/1.11 |
| 2006/0121218 A1 * | 6/2006 | Obara et al. | 428/34.7 |
| 2006/0129175 A1 * | 6/2006 | Griffin et al. | 606/192 |
| 2006/0142696 A1 | 6/2006 | Kumoyama et al. | |
| 2006/0224112 A1 | 10/2006 | Lentz | |
| 2007/0049902 A1 | 3/2007 | Griffin et al. | |
| 2007/0088323 A1 | 4/2007 | Campbell et al. | |
| 2007/0112407 A1 | 5/2007 | Mertens et al. | |
| 2007/0135763 A1 | 6/2007 | Musbach et al. | |
| 2007/0142821 A1 | 6/2007 | Hennessy et al. | |
| 2008/0086191 A1 | 4/2008 | Valencia et al. | |
| 2008/0287786 A1 | 11/2008 | Lentz | |
| 2008/0288041 A1 | 11/2008 | Holman et al. | |
| 2012/0197381 A1 * | 8/2012 | Sims et al. | 623/1.11 |
| 2013/0189190 A1 * | 7/2013 | Wang | 424/9.454 |
| 2014/0025153 A1 * | 1/2014 | Baba | 623/1.11 |

(56) References Cited

U.S. PATENT DOCUMENTS

| | | |
|---|---|---|
| 2014/0081134 A1* | 3/2014 | Fortson et al. .............. 600/435 |
| 2014/0180383 A1* | 6/2014 | Loganathan ................. 623/1.11 |
| 2014/0200648 A1* | 7/2014 | Newell et al. ............... 623/1.11 |

FOREIGN PATENT DOCUMENTS

| | | |
|---|---|---|
| EP | 1461108 | 9/2004 |
| JP | 6277296 | 10/1994 |
| JP | 8257128 | 10/1996 |
| JP | 2000116788 | 4/2000 |
| JP | 2001095924 | 4/2001 |
| JP | 2001333984 | 12/2001 |
| JP | 2002536032 | 10/2002 |
| WO | WO 95/24236 | 9/1995 |
| WO | WO 97/44086 | 11/1997 |
| WO | WO 99/55285 | 11/1999 |
| WO | WO 00/24451 | 5/2000 |
| WO | WO 2004/047899 | 6/2004 |
| WO | WO 2006/007137 | 1/2006 |
| WO | WO 2006/113912 | 10/2006 |
| WO | WO 2008/088766 | 7/2008 |
| WO | WO 2010/009399 | 1/2010 |

OTHER PUBLICATIONS

Terumo Corporation Product Sheet, "Heartrail II PTCA Guiding Catheters," dated before Feb. 20, 2009, one sheet.

Terumo Corporation Product Sheet, "Crosswire/Crosswire NT," dated before Feb. 20, 2009, one sheet.

Terumo Corporation Product Sheet, "Runthrough NS PTCA Guide Wire," dated before Feb. 20, 2009, one sheet.

Terumo Corporation Product Sheet, "Ryujin Plus PTCA Dilatation Catheters," dated before Feb. 20, 2009, one sheet.

Terumo Corporation Product Sheet, "Tsunami Coronary Stent," dated before Feb. 20, 2009, one sheet.

* cited by examiner

BALLOON CATHETER

CROSS-REFERENCE TO RELATED APPLICATIONS

This application claims priority under 35 U.S.C. §119 to U.S. Provisional Application Ser. No. 61/154,339 entitled "BALLOON CATHETER" filed Feb. 20, 2009, the entirety of which is incorporated herein by reference.

FIELD

The present disclosure relates generally to medical devices and, more particularly, to catheters having an elongate shaft with a hypotube.

BACKGROUND

The use of intravascular medical devices has become an effective method for treating many types of vascular disease. In general, one or more suitable intravascular devices are inserted into the vascular system of the patient and navigated through the vasculature to a desired target site. Using this method, virtually any target site in the patient's vascular system may be accessed, including the coronary, cerebral, and peripheral vasculature. Examples of therapeutic purposes for intravascular devices include percutaneous transluminal angioplasty (PTA) and percutaneous transluminal coronary angioplasty (PTCA).

When in use, intravascular devices, such as a catheter, may enter the patient's vasculature at a convenient location and then can be advanced over one or more guidewires to a target region in the anatomy. The path taken within the anatomy of a patient may be very tortuous, and as such, it may be desirable to combine a number of performance features in the intravascular device to aid in advancing the catheter over the one or more guidewires.

A number of different elongated medical device structures, assemblies, and methods are known, each having certain advantages and disadvantages. However, there is an ongoing need to provide alternative elongated medical device structures, assemblies, and methods. In particular, there is an ongoing need to provide alternative medical devices including catheters configured to have improved flexibility and/or torqueability to aid in treating a treatment site of a patient, and methods of making and using such structures and/or assemblies.

BRIEF SUMMARY

The disclosure provides design, material, manufacturing method, and use alternatives for medical devices including, for example, balloon catheters and stent delivery systems such as bifurcated stent delivery systems. An example bifurcated stent delivery system may include an elongate shaft including a proximal section, a midshaft section, and a distal section. The proximal section may include a tubular member having a plurality of slots formed therein. The slots may be arranged in one or more sections having differing slot densities. The midshaft section may include a guidewire port in fluid communication with a guidewire lumen formed in the shaft. A main branch balloon may be coupled to the shaft. A side branch balloon may be disposed adjacent to the main branch balloon. A stent may be disposed on the main branch balloon and on the side branch balloon.

Another example bifurcated stent delivery system may include an elongate shaft including a proximal section, a midshaft section, and a distal section. The proximal section may include a tubular member having a plurality of slots formed therein. The slots may be arranged in one or more sections having differing slot depths. The midshaft section may include a guidewire port in fluid communication with a guidewire lumen formed in the shaft. A main branch balloon may be coupled to the shaft. A side branch balloon may be disposed adjacent to the main branch balloon. A stent may be disposed on the main branch balloon and on the side branch balloon.

Another example bifurcated stent delivery system may include an elongate shaft, the shaft including a proximal section, a midshaft, and a distal section. The proximal section may have a plurality of slots formed therein. A seal tube may be disposed adjacent to the proximal section. The distal section of the elongate shaft may include a distal outer tube and a distal inner tube. The distal inner tube may extend distally from the distal outer tube. A main branch balloon may be coupled to the shaft. The main branch balloon may have a proximal waist attached to the distal outer tube and a distal waist attached to the distal inner tube. A side branch balloon may be disposed adjacent to the main branch balloon. A stent may be disposed on the main branch balloon and on the side branch balloon.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
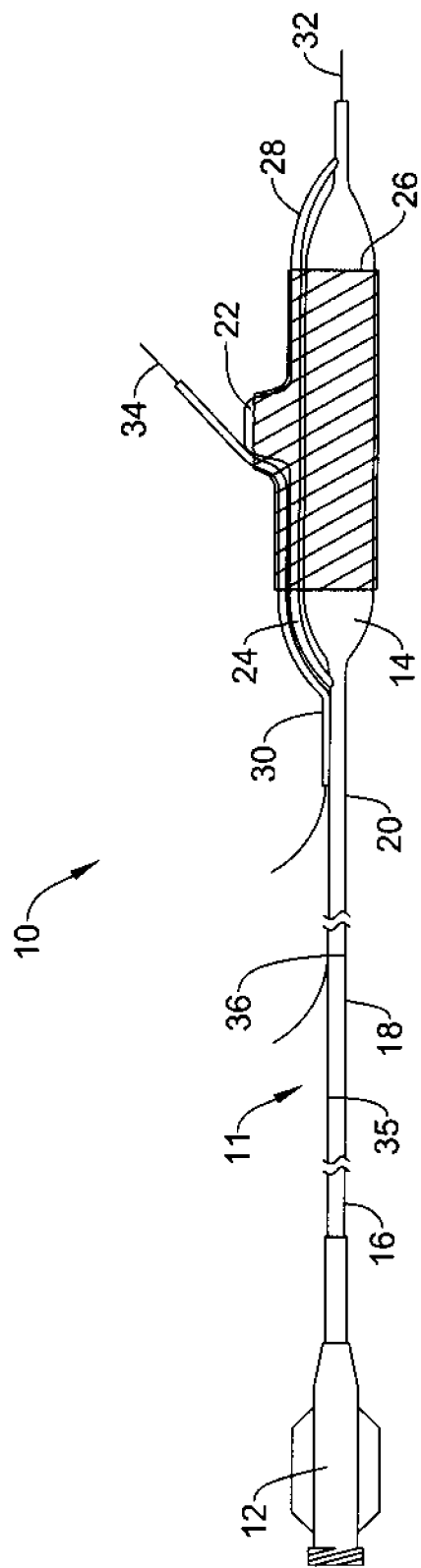
FIG. 1 is a perspective view of an illustrative embodiment of a balloon catheter including a stent for treating a bifurcated vessel.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 is a perspective view of an illustrative embodiment of a balloon catheter 10 including a stent 26 for treating a bifurcated vessel. In the illustrative embodiment, the balloon catheter 10 may be configured to deliver a stent 26 to a bifurcation of a vessel. Although the catheter 10 is illustrated as a balloon catheter for treating a bifurcated vessel, this is not meant to be limiting in any manner and it is contemplated that, in some instances, the catheter 10 can be configured for other medical purposes, as desired. For example, the catheter 10 can be one of a variety of different catheters, such as balloon catheters not necessarily used to treat a bifurcated vessel and/or deploy a stent. For example, an angioplasty balloon catheter and/or a balloon catheter for delivery of a stent to another non-bifurcated vessel. Other contemplated devices may include atherectomy catheters, drug delivery catheters, diagnostic catheters, guide catheters, or any other medical catheter, as desired.

The balloon catheter 10 may include an elongated shaft 11 having a proximal end, a distal end, and one or more lumens extending therebetween. In the illustrative example, the one or more lumens may include an inflation lumen, a guidewire lumen, or any other lumen, as desired. An inflatable main branch balloon 14 may be disposed adjacent to the distal end of the elongated shaft 11. A side branch balloon 22 may be disposed adjacent to the distal end of the elongated shaft 11 adjacent to the main branch balloon 14. As illustrated, the main branch balloon 14 and the side branch balloon 22 may be configured to deliver stent 26. However, it is contemplated that the balloon 14 may be a typical angioplasty or other inflatable member, as desired.

A hub assembly 12 may be connected to the proximal end of the elongated shaft 11 to facilitate connection to an inflation device for inflating/deflating the balloon 14, and/or to facilitate insertion of a guidewire or other medical device therein. In some cases the inflatable balloon 14 may be fluidly connected to the hub assembly 12 via an inflation lumen of the elongated shaft 11.

In some embodiments, the elongate shaft 11 may include one or more sections to help achieve desired pushability, torqueability, and/or flexibility in the elongated shaft 11. The elongate shaft 11 may include a proximal shaft section 16, a midshaft section 18, and/or a distal shaft section 20. The elongate shaft 11, in some embodiments, may include additional shaft sections or regions, or fewer shaft sections or regions, if desired. In some embodiments, the proximal shaft section 16 may be secured to the hub assembly 12 and extend distally therefrom, a proximal portion of the midshaft section 18 may be secured to a distal portion of the proximal shaft section 16 and extend distally therefrom, and a proximal portion of the distal shaft section 20 may be secured to a distal portion of the midshaft section 18 and extend distally therefrom. In some embodiments, the catheter 10 may include a proximal joint 35 between the proximal shaft section 16 and the midshaft section 18 where the midshaft section 18 is joined with the proximal shaft section 16. The catheter 10 may additionally include a main branch guidewire port joint 36 between the midshaft section 18 and the distal shaft section 20 where the distal shaft section 20 is joined with the midshaft section 18. The main branch guidewire port joint 36 may provide access to a guidewire lumen extending through the distal shaft section 20 of the catheter 10.

Figure 2:
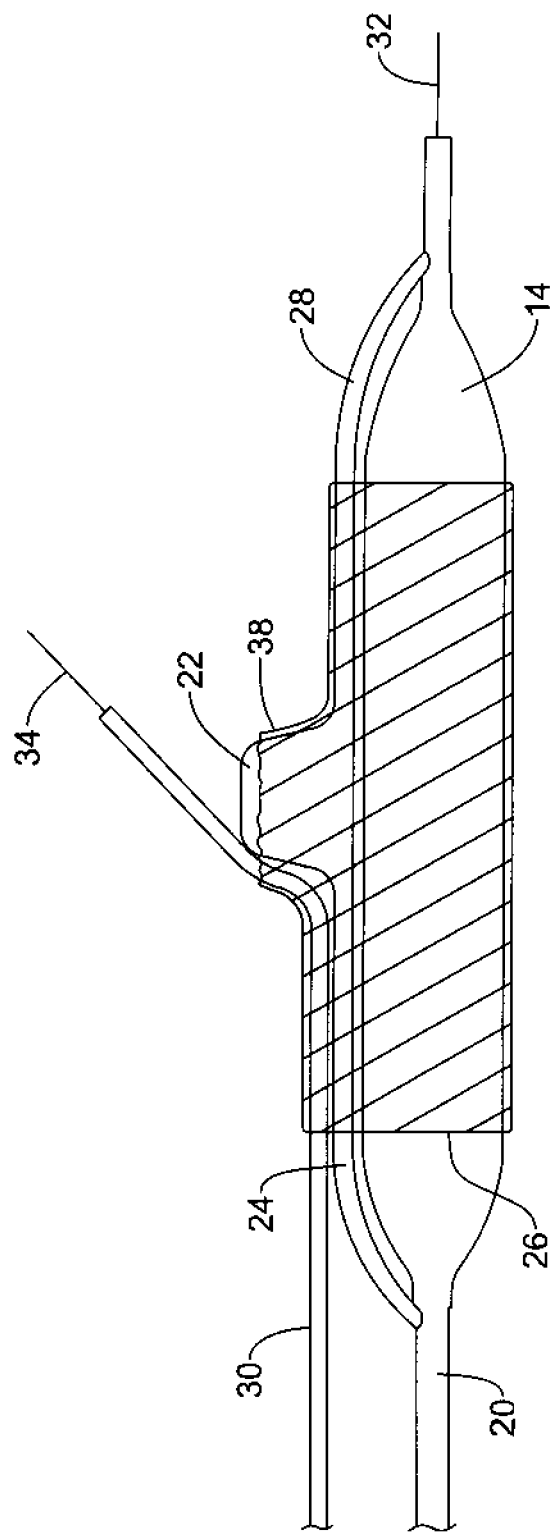
FIG. 2 is a perspective view of an illustrative distal end for the illustrative balloon catheter shown in FIG. 1.

FIG. 2 is a perspective view of an illustrative distal end for the illustrative balloon catheter 10 shown in FIG. 1. In the illustrative embodiment, the main branch balloon 14 may be bonded to the distal region of the distal shaft section 20. The side branch balloon 22 may be connected to the elongate shaft 11 (shown in FIG. 1) by a proximal leg 24 and a distal leg 28. The proximal leg 24 may have a proximal end bonded to the distal shaft section 20 proximal of the main branch balloon 14 or a proximal waist of the main branch balloon 14. A distal leg 28 may have a proximal end bonded to the side branch balloon 22 or be an integral part of the side branch balloon 22 and a distal end bonded to the distal waist of the main branch balloon 14 or to the main branch wire lumen (not shown) distal of the main branch balloon 14.

The catheter 10 may include a secondary tubular member 30 including a proximal end, a distal end, and a secondary guidewire lumen extending therebetween configured to receive a secondary guidewire 34. In some embodiments, the secondary tubular member 30 may be configured to engage a portion of the main branch balloon 14, side branch balloon 22, and/or a portion of the elongated member 11, if desired. The secondary tubular member may be constructed of any of a wide variety of materials including, but not limited to, metal(s), polymer(s), natural rubber, silicone, multilayer materials, urethanes, PEBAX, HDPE, etc.

In some cases, the secondary tubular member 30 may extend through the proximal end of the stent 26 and out a side opening portion 38 of the stent 26. In other cases, the distal end of the secondary tubular member 30 may terminate at the side opening portion 38 of the stent 26 or at a location within the stent 26, as desired.

In some cases, stent 26 may be at least partially constructed of a plurality of interconnected struts, connectors, or other members. The stent 26 defines a proximal opening, a distal opening, and a flow path therebetween. The side opening portion 38 may also be in fluid communication with the flow path, if desired. In some embodiments, the stent 26 may be a bifurcated stent having a trunk and/or stem portion, with one or more leg portions and/or branch openings adjacent thereto, through which the secondary tubular member 30 may be passed. Such bifurcated stents and stent assemblies are well known in the art. In some situations, it is contemplated that the catheter may not include the secondary tubular member 30, if desired.

In the illustrative embodiment, stent 26 may be disposed about at least a portion of main branch balloon 14, side branch balloon 22, and/or secondary tubular member 30. As illustrated, a proximal portion of stent 26 may be disposed about both the main branch balloon 14, side branch balloon 22, and the secondary tubular member 30 and a distal portion of the stent 26 may be disposed about only the main branch balloon 14 and side branch balloon 22. As illustrated, stent 26 may be disposed about the main branch balloon 14 and the side branch balloon 22. In the illustrative embodiment, the stent 26 may include a side opening region configured to be expanded by side branch balloon 22 to engage the ostium of the branching vessel. In this configuration, a distal end of the secondary tubular member 30 may extend through the opening of the stent 26.

In the illustrative embodiment, guidewire 34 may be slidably disposed through the lumen of the secondary tubular member 30. However, in some cases, the guidewire 34 may be merely slid between the main branch balloon 14 or the side branch balloon 22 and the stent 26 without the use of the secondary tubular member 30, if desired. In some embodiments, where the stent 26 is to be positioned substantially proximal to a side branch of the bifurcation, the guidewire 34 and/or secondary tubular member 30 may be configured to extend under the entire length of the stent 26.

Guidewire 32 may be configured to extend through the guidewire lumen of the main branch balloon 14 and extend into the main branch of the vessel. Guidewire 34 may be configured to extend through the secondary tubular member 30 and into the side branch vessel.

In the illustrative dual guidewire embodiment, in operation, the guidewire 32 may be initially advanced through a vessel distal of a side branch of a bifurcation and the secondary guidewire 34 may be advanced through the vessel and into the side branch of the bifurcation. The catheter 10 may then be advanced along the guidewires 32 and 34 through the vessel until the main branch balloon 14, side branch balloon 22, and the stent 26 reach a desired position in the vessel, such as, for example, adjacent to the side branch of the bifurcation. In addition, the main branch balloon 14, side branch balloon 22, and stent 26 may be rotated to align the side opening portion 38 of the stent 26 with the side branch vessel at the bifurcation while being advanced over the guidewires 32 and 34.

Further, it is to be understood that the foregoing balloon catheter 10 and distal end for treating a bifurcated vessel are merely illustrative and are not meant to be limiting in any manner. It is contemplated that the following elongate shafts may be incorporated into any suitable catheter construction including balloon catheters not necessarily configured to treat a bifurcated vessel and/or deploy a stent, atherectomy catheters, drug delivery catheters, diagnostic catheters, guide catheters, as well as any other medical catheter, as desired.

Figure 3:
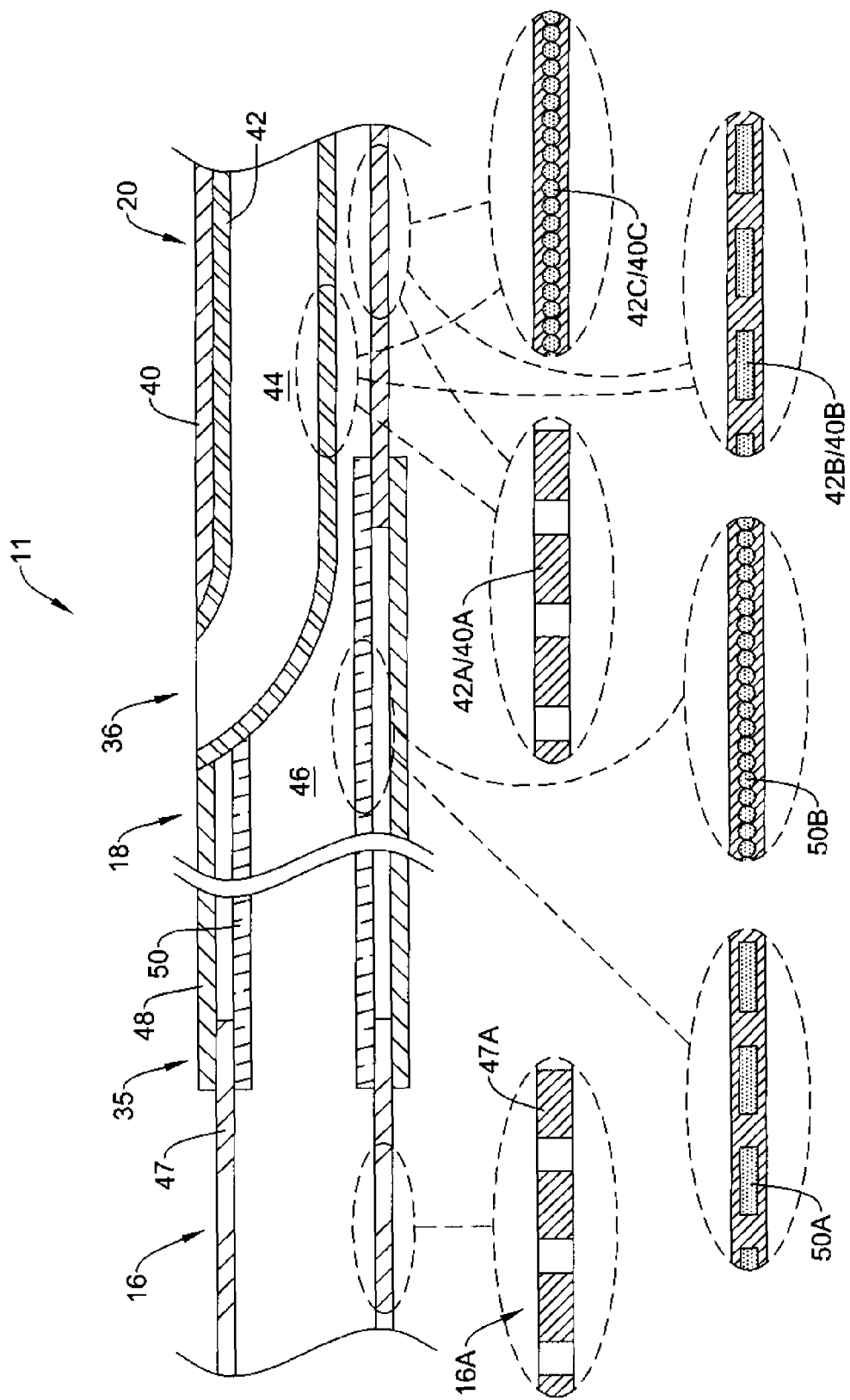
FIG. 3 is a schematic cross-sectional view of an illustrative elongate shaft of an example balloon catheter.

FIG. 3 is a schematic cross-sectional view of an illustrative elongate shaft 11 that may be used, for example, in a balloon catheter like that shown in FIG. 1, or other balloon catheter. The proximal section 16 of the elongated shaft 11 may include an elongated tubular member 47 having a lumen extending therethrough. The proximal shaft section 16 may be bonded to the midshaft 18 at proximal bond 35. The proximal shaft section 16 may be formed of any suitable material. In one embodiment, the proximal shaft section 16 may be a metallic tubular member, such as a hypotube 47A, which may in some embodiments include one or more openings, slots, slits, or other features to provide the metallic tubular member with a desired degree of lateral bending. Examples of hypotubes including one or more openings, slots, slits or other features to provide the metallic tubular member with a desired degree of lateral bending are disclosed in U.S. Pat. Publication No. US 2004/0181174, U.S. Pat. Publication No. US 2007/0135763, U.S. Pat. Publication Nos. 2003/0069522, U.S. Pat. No. 6,579,246, U.S. Pat. No. 6,428,489, and U.S. Pat. No. 6,440,088, which are hereby incorporated by reference. Some examples of suitable metals and metal alloys that may be used for proximal shaft section 16 (and/or other portions of shaft 11) can include stainless steel, such as 304V, 304L, and 316L stainless steel; nickel-titanium alloy such as a superelastic (i.e., pseudoelastic) or linear elastic nitinol; nickel-chromium alloy; nickel-chromium-iron alloy; cobalt alloy; tungsten or tungsten alloys; tantalum or tantalum alloys, gold or gold alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); or the like; or other suitable metals, or combinations or alloys thereof. In some embodiments, it may be desirable to use metals, or metal alloys that are suitable for metal joining techniques such as welding, soldering, brazing, crimping, friction fitting, adhesive bonding, etc. In some cases, a sheath, coating, inner tubular member, liner, or other layer or structure can be used to define a lumen, such as an inflation lumen for example, that may be fluidly sealed between the proximal end of the proximal section 16 and the distal end of the proximal section 16.

In the illustrative embodiment, the midshaft section 18 of the elongate shaft 11 may be disposed distally of the proximal section 16. For example, the midshaft 18 may include a proximal end disposed adjacent to the distal end of the proximal section 16, a distal end, and one or more lumens extending therethrough. In some cases, the proximal end of the midshaft section 18 may be coupled to or otherwise connected to the distal end of the proximal section 16. As illustrated, the midshaft section 18 of the elongate shaft 11 may include an outer tubular member 48 disposed around an inner tubular member 50.

In some cases, the inner tubular member 50 may be formed of a thermoset polymeric material, such as a thermoset polyimide, in some embodiments. In other embodiments, however, the inner tubular member 50 may be formed of another relatively stiff material, such as polyurethane, polyethylene terephthalate (PET), polyoxymethylene blended with a polyether polyester (such as ARNITEL® available from DSM Engineering Plastics or HYTREL® available from DuPont), polyoxymethylene (such as Delrin™ commercially available from DuPont Wilmington, Del.), and the like. The inner tubular member 50 may provide the midshaft section 18 with a degree of rigidity in order to enhance the pushability and torqueability of the midshaft section 18 of the elongate shaft 11. In some embodiments, the inner tubular member 50 can further include a braid 50A or coil 50B to increase flexibility and kink resistance of the midshaft section 18 during torque, but this is not required. In one example embodiment, the midshaft section 18 inner tubular member 50 may be include a metal wire braid 50A encapsulated by a polymer.

The outer tubular member 48 may be formed of a thin, thermoplastic polymeric material. Some example materials may include, but are not limited to, polyamide, polyether block amide, polyurethane, silicone rubber, nylon, polyethylene, fluorinated hydrocarbon polymers, and the like. For example, in some particular examples the outer tubular member 48 is 100% polyamide 6, polyamide 12, or thermoplastic polyurethane. Some polymer materials suitable for use in the outer tubular member 48 are sold under the trademarks of PEBAX, PELLETHANE, TEXIN and Vestamid.

In the illustrative embodiment, the distal section 20 of the elongate shaft 11 may be disposed distally of the midshaft section 18. For example, the distal section 20 may include a proximal end disposed adjacent to the distal end of the midshaft section 18, a distal end, and one or more lumens 44 and 46 extending therethrough. The distal shaft section 20 of the elongate shaft 11 may include an outer tubular member 40 and an inner tubular member 42 extending through the outer tubular member 40. In some cases, the main branch balloon (for example, as shown as 14 in FIGS. 1 and 2) may include a proximal waist bonded to the outer tubular member 40 and a distal waist bonded to the inner tubular member 42, but this is not required.

The inner tubular member 42 may define a guidewire lumen 44 configured to receive a guidewire therethrough. A proximal end of the distal inner tubular member 42 may be exposed to define a main branch guidewire port 36 at the joint between the midshaft section 18 and the distal section 20 of the elongate shaft 11. A guidewire (for example, as shown as guidewire 32 in FIG. 1) may extend through the guidewire lumen 44 and pass through the distal section 20 of the elongate shaft 11 and then exterior to the elongate shaft 11 at the guidewire port joint 36.

The space between the outer surface of the inner tubular member 42 and the inner surface of the outer tubular member 40 may define an inflation lumen 46 in fluid communication with one or more balloons (for example, balloon 14 and/or 22 as shown in FIG. 2) to deliver an inflation fluid to the balloon(s) in order to inflate the balloon(s) during a medical procedure. Although not shown, it is contemplated that if multiple balloons are present, the catheter may include separate inflation lumens to provide independent inflation of the multiple balloons, if desired.

The inner tubular member 42 may include and/or be made of any of a broad variety of materials and/or structures. The inner tubular member 42 may have a single-layer tubular construction or a multi-layer tubular construction, or a combination thereof. For example, the inner tubular member 42 may be a single tubular member formed by a single layer of material, or in other embodiments, may be formed by a plurality of tubular members and/or a plurality of layers of material that may be the same and/or different, but in combination form the inner tubular member 42.

In some embodiments, the inner tubular member 42 may include a flexible polymer, for example a polymer material having a durometer in the range of about 5 D to about 90 D. For example, the outer layer can include or be made up of one or more tubular segments of a polyamide, such as polyamide 12, polyether block amide (PEBA), a polyether-ester elastomer, or other similar material. In some cases, the inner tubular member 42 may be lined with a lubricious polymer such as high density polyethylene (HDPE) or polytetrafluoroethylene (PTFE), for example, or a copolymer of tetrafluoroethylene with perfluoroalkyl vinyl ether (PFA) (more specifically, perfluoropropyl vinyl ether or perfluoromethyl vinyl ether), or the like. In some particular embodiments, the inner tubular member 42 may be formed of Marlex® HDPE, which can extend the length of the inner tubular member 42. In some cases, a tie layer can be provided to the inner tubular member 42 to bond the lubricious layer to the inner tubular member 42, may be a low density polyethylene (LDPE), such as a modified LDPE. In one particular embodiment, the inner tubular member 42 may be a co-extruded three-layer shaft segment including an inner layer of high density polyethylene (HDPE, namely Marlex® 4903), an outer layer of polyether block amide (PEBA, namely Pebax® 7233) and a tie-layer of Plexar® 380 to adhere the layers. Plexar® 380 is a known commercially available tie layer material which is a modified low density polyethylene.

In other embodiments, the inner tubular member 42 may be from a fluorinated ethylene propylene (FEP) lined thermoset polymeric material, such as a thermoset polyimide, polyurethane, polyethylene terephthalate (PET), polyoxymethylene blended with a polyether polyester (such as ARNITEL® available from DSM Engineering Plastics or HYTREL® available from DuPont), polyoxymethylene (such as Delrin™ commercially available from DuPont Wilmington, Del.), and the like. The FEP may help to attain wire movement in the lumen 44. In some embodiment, the inner tubular member 42 can further include a braid 42B or coil 42C to increase flexibility and kink resistance of the distal section 20 during torque. In this example, the torque performance may be increased as the inner tubular member 42 may extend to the distal tip of the catheter. However, in some cases, the distal portion of the catheter 10 under the balloon can be relatively stiff. To help reduce the stiffness, the portion of the inner tubular member 42 may be processed to include one or more bends, slits, or holes filled with a more flexible material to increase flexibility. Further, any other suitable method of increasing flexibility may be used, as desired.

In one embodiment, the outer tubular member 40 may be formed of any desired polymer material, such as a thermoplastic polymer. For instance, some suitable thermoplastic materials include polyamide, such as polyamide 6, polyamide 12, or polyamide 612, and polyether block amide (PEBA). In one particular embodiment, the outer tubular member 70 may be a PEBA having a durometer hardness of 70 D (e.g., Pebax® 7033). Other suitable polymer materials include those listed above regarding the inner tubular member 42.

In another embodiment, the outer tubular member 40 may be formed of a thermoset polymeric material, similar to the inner tubular member 50 of the midshaft 18, such as a thermoset polyimide. In other embodiments, however, the outer tubular member 40 may be formed of another relatively stiff material, such as polyurethane, polyethylene terephthalate (PET), polyoxymethylene blended with a polyether polyester (such as ARNITEL® available from DSM Engineering Plastics or HYTREL® available from DuPont), polyoxymethylene (such as Delrin™ commercially available from DuPont Wilmington, Del.), and the like. In some embodiment, the outer tubular member 40 can further include a braid 40B or coil 40C to increase flexibility and kink resistance of the distal section 20 during torque.

In an alternative embodiment, the outer tubular member 40 and/or the inner tubular member 42 can include a tubular member, such as a nickel-titanium hypotube 40A and 42A, which may in some embodiments include one or more openings, slots, slits, or other features to provide the tubular member with a desired degree of lateral bending. The nickel-titanium hypotube 40A and 42A can be superelastic (i.e., pseudoelastic) or linear elastic nitinol. In some cases, the hypotube 40A and 42A can be processed to be more flexible, as is well known in the art. Examples of hypotubes that may be used are disclosed in U.S. Pat. Publication No. US 2004/0181174, U.S. Pat. Publication No. US 2007/0135763, U.S. Pat. Publication Nos. 2003/0069522, U.S. Pat. No. 6,579,246, U.S. Pat. No. 6,428,489, and U.S. Pat. No. 6,440,088, which are hereby incorporated by reference.

Figure 4:
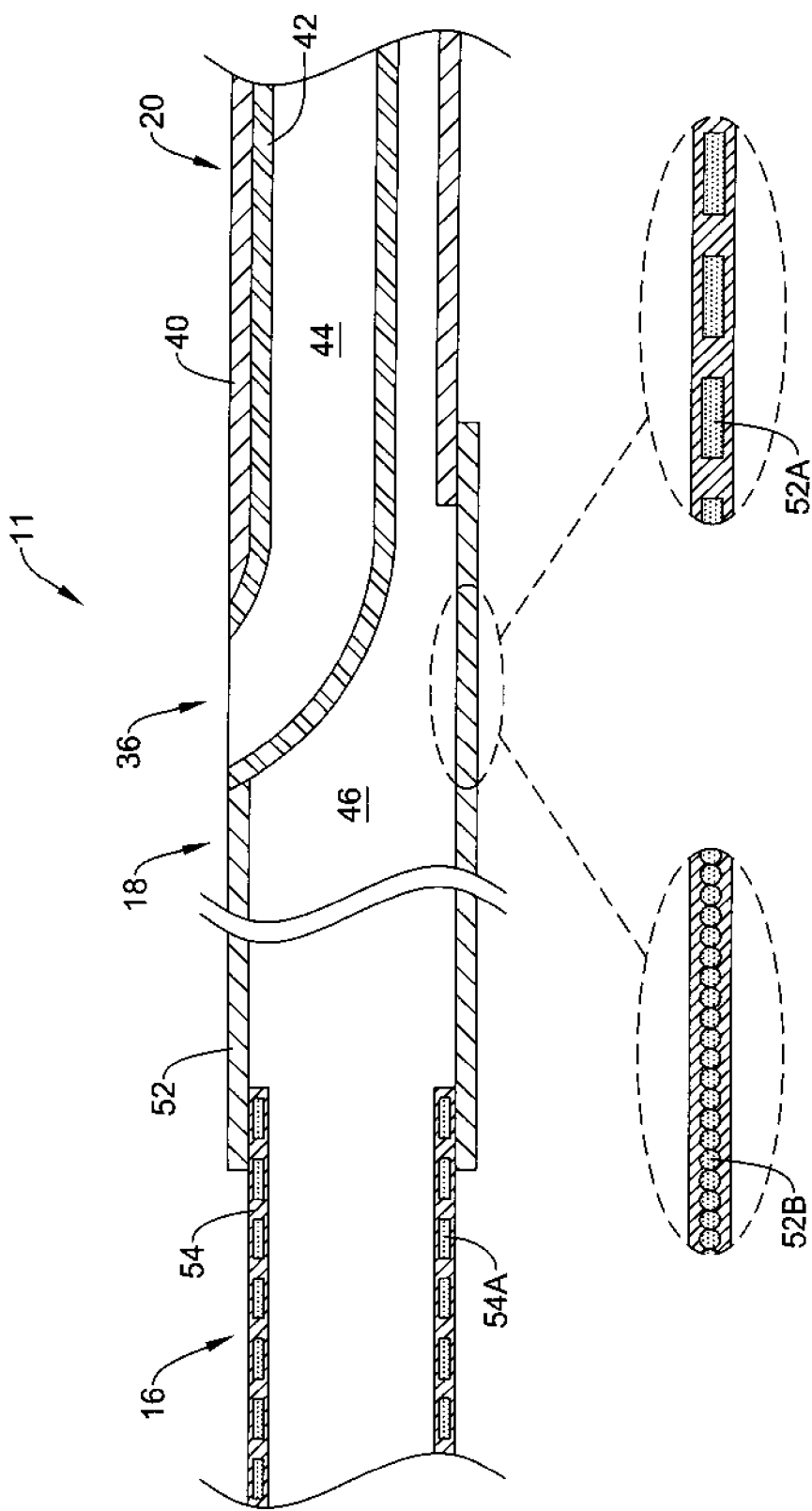
FIG. 4 is a schematic cross-sectional view of another illustrative elongate shaft of an example balloon catheter.

FIG. 4 is a schematic cross-sectional view of another illustrative elongate shaft 11 of a balloon catheter, which may be used, for example, in a balloon catheter configuration like that shown in FIG. 1, or other configurations. In the illustrative elongate shaft 11, the midshaft 18 may include only tubular member 52. Tubular member 52 may be formed of a thermoset polymeric material, such as a thermoset polyimide, in some embodiments. In other embodiments, however, the tubular member 52 may be formed of another relatively stiff material, such as polyurethane, polyethylene terephthalate (PET), polyoxymethylene blended with a polyether polyester (such as ARNITEL® available from DSM Engineering Plastics or HYTREL® available from DuPont), polyoxymethylene (such as Delrin™ commercially available from DuPont Wilmington, Del.), and the like. In some embodiment, the tubular member 52 can further include a braid 52A or a coil 52B to increase flexibility and kink resistance of the midshaft section 18 during torque, but this is not required. For example, the midshaft section 18 tubular member 52 can include a braid 52A encapsulated in a polymer.

In other embodiments, the tubular member 52 may be formed of a thin, thermoplastic polymeric material. Some example materials may include, but are not limited to, polyamide, polyether block amide, polyurethane, silicone rubber, nylon, polyethylene, fluorinated hydrocarbon polymers, and the like. For example, in some particular examples the tubular member 52 is 100% polyamide 6, polyamide 12, or thermoplastic polyurethane. Some polymer materials suitable for use in the tubular member 52 are sold under the trademarks of PEBAX, PELLETHANE, TEXIN and Vestamid.

In the illustrative embodiment, the proximal section 16 may include a tubular member 54 formed from a polymer metal composite. For example, the tubular member 54 may include a metal wire braid 54A encapsulated in a polymer. Further, it is contemplated that the polymer metal composite may be a metal coil encapsulated by a polymer, similar to other embodiments discussed above. Some examples of some suitable polymers can include, but are not limited to, polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysulfone, nylon, perfluoro (propyl vinyl ether) (PFA), polyether-ester, polymer/metal composites, etc., or mixtures, blends or combinations thereof.

In some cases, the polymer metal composite may have a relatively lower stiffness than a stainless steel hypotube and may have lower normal forces acting on the tubular member 54 in a tortuous path. In some cases, the polymer metal composite tubular member 54 can be made of a larger diameter than a stainless steel hypotube without having the increase in stiffness, as would result in the stainless steel hypotube. A larger diameter may allow the polymer metal composite tubular member 54 to have a greater moment of inertia than the stainless steel hypotube which, in some cases, can improve torque control. Additionally, the proximal metal composite tubular member 54 may be heat welded to the midshaft removing the need for an adhesive bond between the is proximal section 16 and the midshaft section 18, as is typically needed for a stainless steel hypotube.

Additionally, it is contemplated that tubular member 54 may be used in combination with the structure of the embodiment shown in FIG. 3 instead of tubular member 47 for the proximal section 47 of the elongate shaft 11, as desired.

Figure 5:
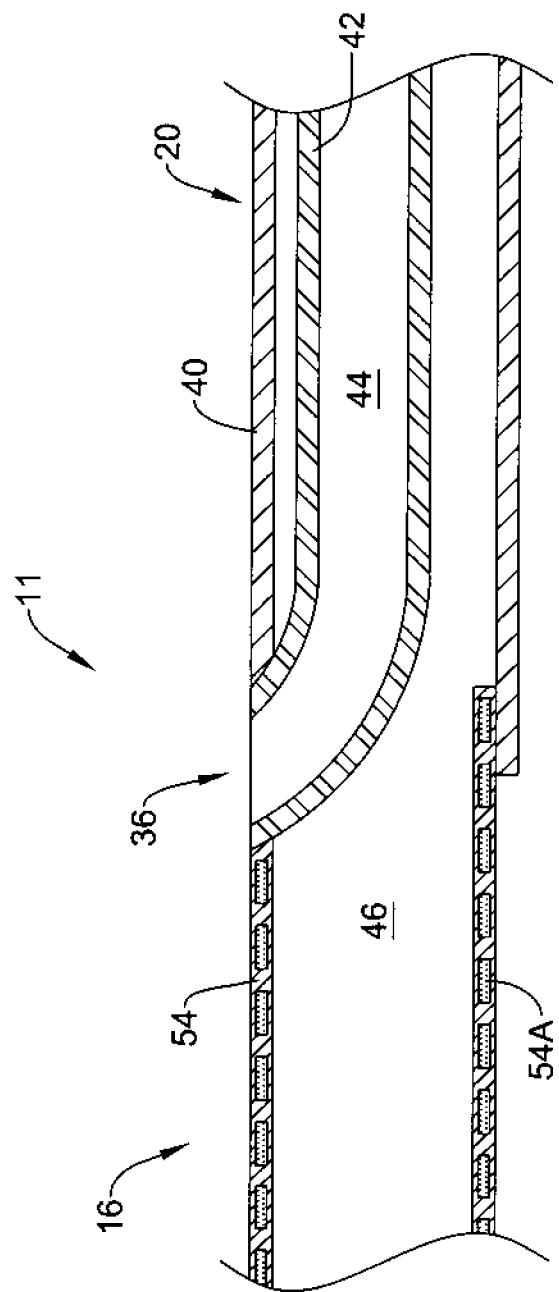
FIG. 5 is a schematic cross-sectional view of another illustrative elongate shaft of an example balloon catheter.

FIG. 5 is a schematic cross-sectional view of another illustrative elongate shaft 11 of a balloon catheter, which may be used in a balloon catheter construction similar to that shown in FIG. 1, or other constructions. In the illustrative embodiment, the midshaft section 18 has been removed from the catheter 10 and the tubular member 54 of the proximal section 16 can extend all the way to the main branch guidewire port 36 joint. The metal polymer composite used for tubular member 54 may provide a sufficient flexibility to track the vessel lumen and/or delivery catheter, as desired.

Additionally, it is contemplated that the midshaft section 18 can be provided in the illustrative embodiment, but can be formed of the same or similar metal polymer composite as tubular member 54. Tubular member 54 may be constructed of more than one material or of one material of multiple durometers, as is known in the art, to achieve different stiffness at different portions of the shaft. For example, the portion of tubular member 54 that may reside in the guide catheter curve during PTCA procedure could be more flexible, due to its increased tortuosity, than the proximal portion that typically resides in the relatively less tortous abdominal aorta.

In the illustrative embodiment, the elongate shaft 11 may be configured to impart desired flexibility, torqueability, and kink resistance to the balloon catheter 10. In some applications, such as, for example, when advancing the balloon catheter over one or more guidewires, the distal end of the balloon catheter 10 may need to be rotated, for example, in a bifurcated system, to align with the vessel bifurcation and/or to track across wire crosses. To do this, the physician, medical technician, or other user may rotate the proximal end of the balloon catheter 10. However, with some catheter systems, when the balloon catheter is in a tortuous passage, the distal end of the balloon catheter 10 may not be responsive to the rotations at the proximal end (i.e does not rotate), the rotations may not be efficient (i.e. ten proximal rotations to one distal rotation), or the distal end can lag or whip. There may also be structures in non-bifurcated systems to rotate the catheter as well.

The torqueability of the elongate shaft 11 of the balloon catheter 10 may relate to the moment of torque that is placed about a longitudinal axis of the elongate shaft 11. As such, the torqueability may be directly related to the shear modulus and the moment of inertia of the elongate shaft 11. As such, the greater the shear modulus of the elongate shaft 11, the greater the torqueability of the elongate shaft 11. Similarly, the greater the moment of inertia of the elongate shaft 11, the greater the torqueability of the elongate shaft 11.

For mere simplicity, the torqueability will be described with reference to tensile modulus, which is related to shear modulus, and wall thickness and O.D., which is related to the moment of inertia for a given material. In one example elongate shaft 11, a sufficient torqueability may be achieved with a polyimide material having a tensile modulus of at least 3000 megapascals (MPa) and a wall thickness of at least 0.002 inches and an O.D. in the range of 0.01 to 0.1 inches. As the tensile modulus increases, a thinner wall thickness may be employed. Similarly, as the wall thickness is increased, a smaller tensile modulus may be used. Further, it is contemplated that a tensile modulus of at least 2000 MPa, at least 3000 MPa, at least 4000 MPa, or other tensile modulus may be used with an appropriate wall thickness, as desired.

Figure 6:
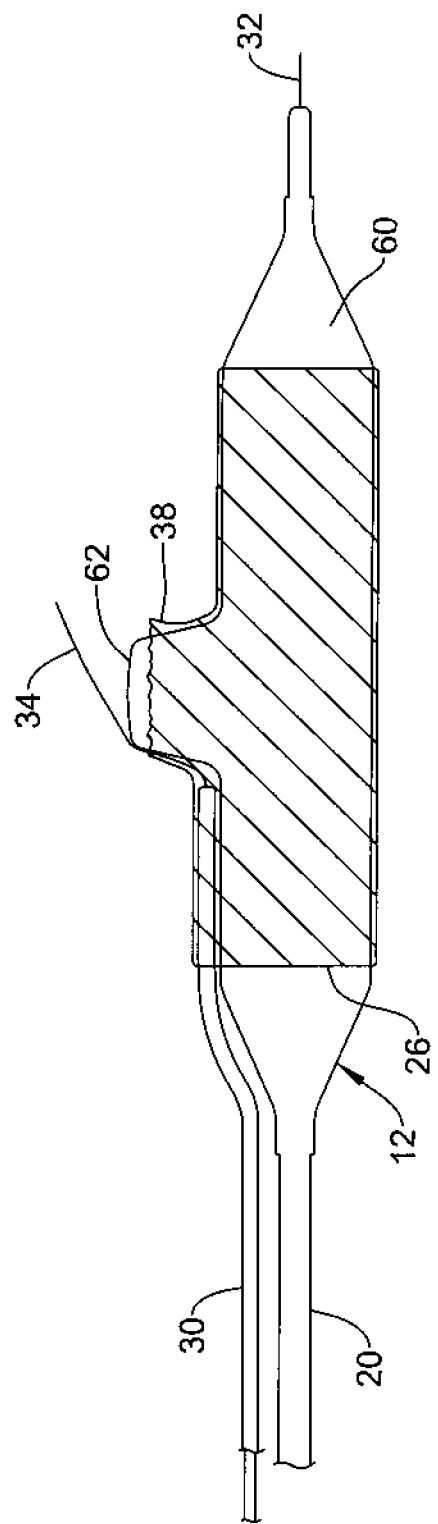
FIG. 6 is a perspective view of an illustrative distal end for another example embodiment a balloon catheter.

FIG. 6 is a perspective view of another illustrative distal end that may be disposed at the distal end of an elongate shaft 11 in a balloon catheter. The illustrative distal end may be similar to the distal end shown in FIG. 2 with the main branch balloon 14 and side branch balloon 22 replaced with a single balloon 60. As illustrated, balloon 60 may include a bulge portion 62 that may be configured to extend into and expand the side opening portion 38 of the stent 26, similar to side branch balloon 22.

As illustrated, the distal end of the side branch tubular member 30 may have a distal end terminating at a location under the stent 26. However, it is contemplated that the side branch tubular member 30 may have a distal end extending distally through the side opening portion 38 of the stent 26, similar to FIG. 2, or may terminate at a location under the stent 26, as desired.

In the illustrative embodiment, stent 26 may be disposed about at least a portion of balloon 60 and/or secondary tubular member 30. As illustrated, a proximal portion of stent 26 may be disposed about both the balloon 60 and the secondary tubular member 30 and a distal portion of the stent 26 may be disposed about only the balloon 60.

Figure 7:
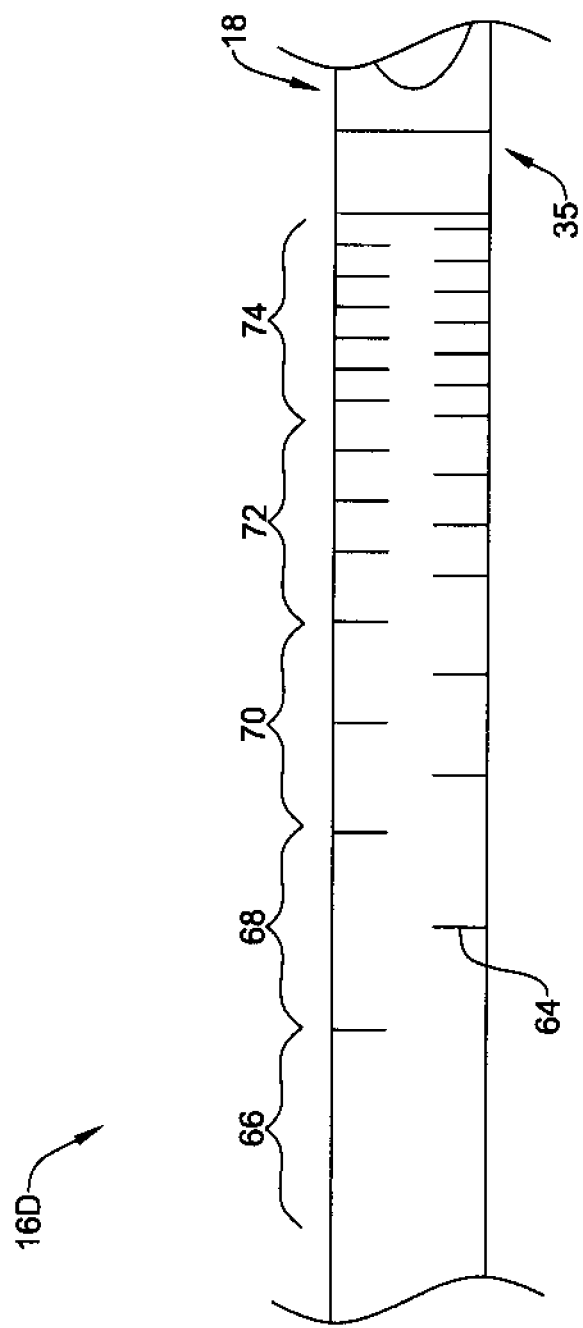
FIG. 7 is a top view of a portion of another illustrative shaft of an example balloon catheter.

FIG. 7 is a top view of a portion of another illustrative shaft 11 that may be utilized in a balloon catheter. Elongate shaft 11 may include proximal shaft section 16D that may be similar to the proximal shaft section(s) 16 disclosed herein and may include any suitable materials including those disclose herein (e.g., stainless steel, nickel-titanium alloy, etc.). Proximal shaft section 16D may have a plurality of slots, slits, or openings 64 formed therein. Proximal shaft section 16D may also include a sleeve or sheath (not shown) that may be disposed along the interior, exterior, or both of proximal shaft section 16D. The sleeve may substantially seal proximal shaft section 16D so as to prevent fluids or gasses from passing through slots 64. Proximal shaft portion 16D may also include a core member of shaft (not shown) disposed therein that is attached to proximal shaft section 16D and extends through midshaft 18. Core member may be formed of a tempered stainless steel wire (or any other suitable material) and may gradually decrease in outer diameter (and, thus, flexibility). Some discussion of a core member that may be suitable for balloon catheter 10 can be found in U.S. patent application Ser. No. 12/389,393, filed on Feb. 20, 2009, the entire disclosure of which is herein incorporated by reference.

In general, slots 64 may be configured to provide proximal shaft section 16D with the desired flexibility characteristics. For example, slots 64 may increase the flexibility of proximal shaft section 16D such that a less abrupt transmission may occur between proximal shaft section 16D and other components of shaft 11. In some examples, slots 64 may be disposed along essentially the entire length of proximal shaft section 16D. In some other examples, one or more regions, such as a region 66, may lack slots 64 altogether. One or more additional sections may be defined in proximal shaft section 16D that includes slots 64 disposed in differing densities. The densities of slots 64 may increase in the distal direction so that proximal shaft portion 16D may be more flexible distally (e.g., as it approaches bond 35 and/or midshaft 18). For example, proximal shaft portion 16D may include a first slot density region 68, a second slot density region 70 that has slots 64 with a greater slot density than in region 68, a third slot density region 72 that has slots 64 with a greater slot density than in region 70, and a fourth slot density region 74 that has slots 64 with a greater slot density than in region 72. This arrangement may define a flexibility that corresponds to slot density (e.g., the greater the slot density the greater the flexibility) and that forms a smooth transition to other portions of shaft 11. Proximal shaft portion 16D may also include one or more additional regions having slots 64 with the same or different slot densities. Further, it is contemplated that any number of slot density regions may be used, as desired.

Figure 8:
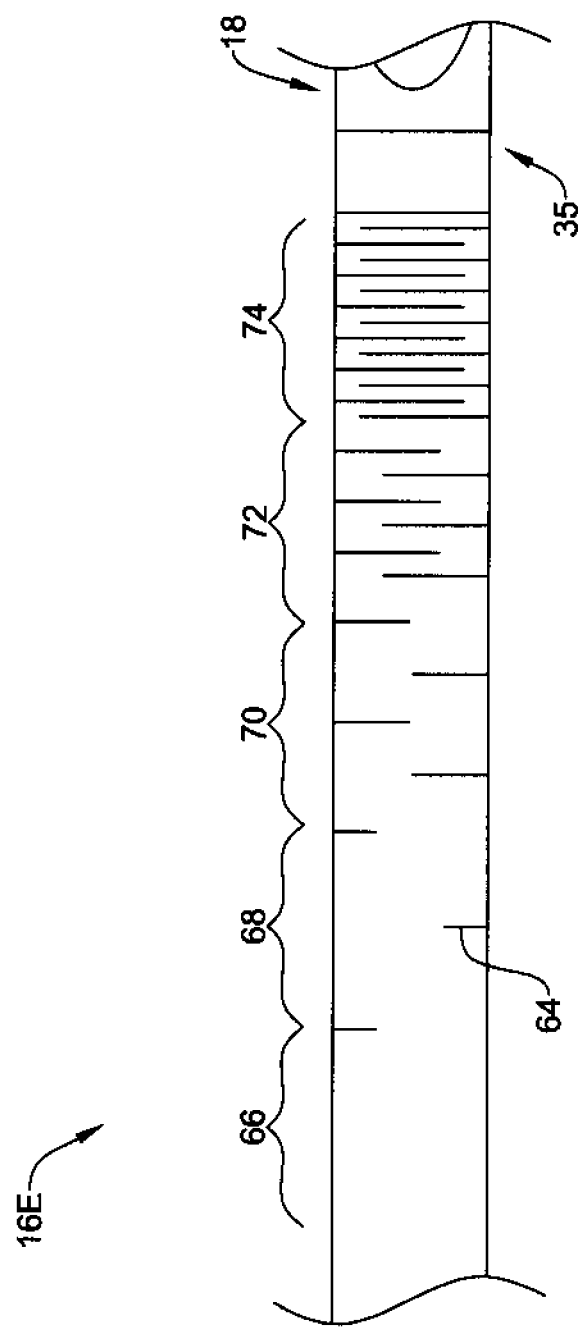
FIG. 8 is a top view of a portion of another illustrative shaft of an example balloon catheter.

Other variations in slot 64 configuration are also contemplated. For example, FIG. 8 illustrates a proximal shaft section 16E may include variations in slots depth (and/or slot length). In this example, region 68 may have slot(s) 64 with a first slot depth, region 70 may have slot(s) 64 with a greater slot depth than in region 68, region 72 may have slot(s) 64 with a greater slot depth than in region 70, and region 74 may have slot(s) 64 with a greater slot depth than in region 72. This arrangement may define a flexibility that corresponds to slot depth (e.g., the greater the slot depth the greater the flexibility) and that forms a smooth transition to other portions of shaft 11. Proximal shaft portion 16E may also include one or more additional regions having slots 64 with the same or different slot depths, as desired. Further, it is contemplated that any suitable number of slot depth regions may be used, as desired. Examples may be disclosed in U.S. Pat. Publication No. US 2004/0181174, U.S. Pat. Publication No. US 2007/0135763, U.S. Pat. Publication Nos. 2003/0069522, U.S. Pat. No. 6,579,246, U.S. Pat. No. 6,428,489, and U.S. Pat. No. 6,440,088, which are hereby incorporated by reference.

In at least some embodiments, portions or all of the catheters, or other components that are part of or used in the device, may be doped with, made of; or otherwise include a radiopaque material. Radiopaque materials are understood to be materials capable of producing a relatively bright image on a fluoroscopy screen or another imaging technique during a medical procedure. This relatively bright image aids the user of devices in determining its location. Some examples of radiopaque materials can include, but are not limited to, gold, platinum, palladium, tantalum, tungsten alloy, polymer material loaded with a radiopaque filler, and the like. Additionally, radiopaque marker bands and/or coils may be incorporated into the design of catheters to achieve the same result.

In some embodiments, a degree of MRI compatibility is imparted into catheters. For example, to enhance compatibility with Magnetic Resonance Imaging (MRI) machines, it may be desirable to make the elongated shaft 11, main branch balloon 14, side branch balloon 22, and/or inflatable balloon 60, or other portions of the medical devices, in a manner that would impart a degree of MRI compatibility. For example, elongated shaft 11, main branch balloon 14, side branch balloon 22, and/or inflatable balloon 60, or portions thereof, may be made of a material that does not substantially distort the image and create substantial artifacts (artifacts are gaps in the image). Certain ferromagnetic materials, for example, may not be suitable because they may create artifacts in an MRI image. Elongated shaft 11, main branch balloon 14, side branch balloon 22, and/or inflatable balloon 60, or portions thereof; may also be made from a material that the MRI machine can image. Some materials that exhibit these characteristics include, for example, tungsten, Elgiloy, MP35N, nitinol, and the like, and others.

In some embodiments, a sheath and/or coating, for example a lubricious, a hydrophilic, a protective, or other type of material may be applied over portions or all of the elongated shaft 11, main branch balloon 14, side branch balloon 22, and/or inflatable balloon 60, or other portions of devices.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. Further, it is contemplated that the various features and components of the foregoing embodiments can be mixed and matched as desired. It should be understood that this disclosure is, in many respects, only illustrative. Changes may be made in details, particularly in matters of shape, size, and arrangement of steps without exceeding the scope of the invention. For example, although set forth with specific reference to catheters in some of the example embodiments shown in the Figures and discussed above, the invention may relate to virtually any medical device that may aid a user of the device in advancing a device in a vessel. Thus, while the Figures and descriptions above are directed toward a catheter, in other applications, sizes in terms of diameter, width, and length may vary widely, depending upon the desired properties of a particular device. The scope of the invention is, of course, defined in the language in which the appended claims are expressed.

What is claimed is:

1. A bifurcated stent delivery system, comprising:
an elongate shaft including a proximal section defined by a tubular member, a midshaft section, and a distal section;
wherein a proximal end of the midshaft section is coupled to a distal terminal end of the proximal section tubular member by an outer tubular member disposed around the elongate shaft and an inner tubular member disposed inside the elongate shaft;
wherein the proximal section includes a tubular member having a plurality of slots formed therein, wherein the slots are arranged in one or more sections having differing slot densities, wherein the slots are arranged in two or more axially spaced circumferential sections within the proximal section, the slots in axially adjacent sections having differing slot depths;
wherein the midshaft section includes a guidewire port in fluid communication with a guidewire lumen formed in the shaft, wherein the distal terminal end of the proximal section tubular member is proximal of the midshaft guidewire port;
a main branch balloon coupled to the shaft;
a side branch balloon disposed adjacent to the main branch balloon; and
a stent disposed on the main branch balloon and on the side branch balloon.

2. The bifurcated stent delivery system of claim 1, wherein the proximal section includes a sheath disposed along an interior surface, an exterior surface, or both of the tubular member to substantially seal the proximal shaft section.

3. The bifurcated stent delivery system of claim 1, wherein the one or more sections having differing slot densities includes a first section and a second section disposed distally of the first section.

4. The bifurcated stent delivery system of claim 3, wherein the second section has a greater slot density than the first section.

5. The bifurcated stent delivery system of claim 4, wherein the one or more sections having differing slot densities further comprises a third section having a greater slot density than the second section.

6. The bifurcated stent delivery system of claim 1, wherein the one or more section having different slot densities forms a smooth transition in flexibility between the proximal shaft and the midshaft.

7. A bifurcated stent delivery system, comprising:
an elongate shaft including a proximal section, a midshaft section, and a distal section; wherein the proximal section includes a tubular member having a plurality of slots formed therein, each slot having a depth, wherein the slots are arranged in two or more axially spaced circumferential sections within the proximal section, wherein all of the slots in a circumferential section have the same depth, the slots in axially adjacent sections having differing slot depths;
wherein the midshaft section includes a guidewire port in fluid communication with a guidewire lumen formed in the shaft;
a main branch balloon coupled to the shaft;
a side branch balloon disposed adjacent to the main branch balloon; and
a stent disposed on the main branch balloon and on the side branch balloon.

8. The bifurcated stent delivery system of claim 7, wherein the proximal section includes a sheath disposed along an interior surface, an exterior surface, or both of the tubular member to substantially seal the proximal shaft section.

9. The bifurcated stent delivery system of claim 7, wherein the one or more sections having differing slot depths includes a first section and a second section disposed distally of the first section.

10. The bifurcated stent delivery system of claim 9, wherein the second section has a greater slot depth than the first section.

11. The bifurcated stent delivery system of claim 10, wherein the one or more sections having differing slot depths further comprises a third section having a greater slot depth than the second section.

12. The bifurcated stent delivery system of claim 7, wherein the one or more section having different slot depths forms a smooth transition in flexibility between the proximal shaft and the midshaft.

* * * * *